(12) United States Patent
Palagi (10) Patent No.: US 12,144,523 B2
(45) Date of Patent: Nov. 19, 2024

(54) HEAD OVER HEAD CONNECTOR ASSEMBLY

(71) Applicant: Life Spine, Inc., Huntley, IL (US)

(72) Inventor: Gregory Palagi, Geneva, IL (US)

(73) Assignee: Life Spine, Inc., Huntley, IL (US)

( * ) Notice: Subject to any disclaimer, the term of this patent is extended or adjusted under 35 U.S.C. 154(b) by 981 days.

(21) Appl. No.: 17/150,462

(22) Filed: Jan. 15, 2021

(65) Prior Publication Data

US 2021/0137565 A1    May 13, 2021

Related U.S. Application Data

(63) Continuation-in-part of application No. 16/790,098, filed on Feb. 13, 2020, now Pat. No. 11,350,968, which is a continuation of application No. 15/947,848, filed on Apr. 8, 2018, now Pat. No. 10,588,666.

(60) Provisional application No. 62/483,590, filed on Apr. 10, 2017.

(51) Int. Cl.
  *A61B 17/70*    (2006.01)
  *A61B 17/86*    (2006.01)
  *A61B 90/00*    (2016.01)

(52) U.S. Cl.
  CPC ...... *A61B 17/7032* (2013.01); *A61B 17/7037* (2013.01); *A61B 17/8605* (2013.01); *A61B 17/863* (2013.01); *A61B 2090/037* (2016.02)

(58) Field of Classification Search
  CPC ............ A61B 17/7032; A61B 17/7034; A61B 17/7035; A61B 17/7037; A61B 17/704; A61B 17/8605

USPC ................................ 606/250, 264–266, 278
See application file for complete search history.

(56) References Cited

U.S. PATENT DOCUMENTS

| | | | |
|---|---|---|---|
| 2,910,995 A * | 11/1959 | Jacuzzi | A47B 91/066 248/362 |
| 8,628,558 B2 | 1/2014 | Harvey et al. | |
| 8,852,241 B2 * | 10/2014 | Datta | A61B 17/7049 606/279 |
| 9,707,013 B2 | 7/2017 | Rezach et al. | |
| 9,775,660 B2 | 10/2017 | Brecher et al. | |
| 9,883,892 B2 | 2/2018 | Jackson et al. | |
| 10,588,666 B2 | 3/2020 | Samuel et al. | |
| 2010/0160981 A1 * | 6/2010 | Butler | A61B 17/7049 606/308 |

(Continued)

FOREIGN PATENT DOCUMENTS

EP    2 985 001 A1    2/2016

OTHER PUBLICATIONS

International Search Report for PCT/US2018/026646 Dtd Jun. 25, 2018, 5 pages.

*Primary Examiner* — Eduardo C Robert
*Assistant Examiner* — Christina Negrellirodriguez
(74) *Attorney, Agent, or Firm* — Foley & Lardner LLP (57) ABSTRACT

A connector assembly includes a bone screw including a head, a first holder assembly configured to receive the head of the bone screw from a bottom of the first holder assembly, an extension set screw including a head and a threaded portion, the threaded portion configured to be received from a top of the first holder assembly, a second holder assembly configured to receive the head of the extension set screw, and an end fastener configured to be received by the second holder assembly.

20 Claims, 8 Drawing Sheets

(56) References Cited

U.S. PATENT DOCUMENTS

| | | | |
|---|---|---|---|
| 2011/0106178 A1* | 5/2011 | Schwab | A61B 17/7037 |
| | | | 606/305 |
| 2012/0143266 A1 | 6/2012 | Jackson et al. | |
| 2014/0121703 A1 | 5/2014 | Jackson et al. | |
| 2014/0135839 A1* | 5/2014 | Frankel | A61B 17/00234 |
| | | | 606/279 |
| 2014/0236239 A1 | 8/2014 | Biedermann et al. | |
| 2016/0331412 A1 | 11/2016 | Biedermann et al. | |
| 2018/0228516 A1* | 8/2018 | Armstrong | A61B 17/7035 |

\* cited by examiner

HEAD OVER HEAD CONNECTOR ASSEMBLY

CROSS-REFERENCE TO RELATED PATENT APPLICATIONS

This application is a continuation in part of US application Ser. No. 16/790,098, filed Feb. 13, 2020, which is a continuation of U.S. application Ser. No. 15/947,848, filed Apr. 8, 2018, which claims priority to U.S. Provisional Application No. 62/483,590, filed Apr. 10, 2017, all of which are incorporated herein by reference in their entireties.

BACKGROUND

The present disclosure relates generally to the field of bone screws and connector assemblies usable in connection with spinal fixation or other procedures. It is at times necessary to maintain a desired relationship between, for example, vertebral bodies. One way to accomplish this is to utilize spinal rods and anchoring devices such as bone screws to form one or more connector assemblies.

SUMMARY

One embodiment relates to a connector assembly, including a bone screw comprising a head; a first holder assembly configured to receive the head of the bone screw from a bottom of the first holder assembly; an extension set screw comprising a head and a threaded portion, the threaded portion configured to be received from a top of the first holder assembly; a second holder assembly configured to receive the head of the extension set screw; and an end fastener configured to be received by the second holder assembly.

Another embodiment relates to a connector assembly, including a bone screw comprising a head; a first holder assembly configured to receive the head of the bone screw; an extension set screw comprising a head and a threaded portion, the threaded portion configured to be received by the first holder assembly; a second holder assembly configured to receive the head of the extension set screw; and a set screw configured to be received by the second holder assembly. The first holder assembly and the second holder assembly are configured to secure first and second spinal rods in a generally parallel fashion.

Another embodiment relates to a method of assembling a connector assembly including securing a bone screw to bone, the bone screw including a head and a threaded portion, the threaded portion configured to engage the bone; coupling a first holder assembly to the bone screw, wherein the head of the bone screw is received within the first holder assembly; positioning a first spinal rod within the first holder assembly; coupling an extension set screw to the first holder assembly to secure the first spinal rod in a desired position, the extension set screw comprising a head and a threaded portion, the threaded portion configured to threadingly engage the first holder assembly; coupling a second holder assembly to the extension set screw, wherein the head of the extension set screw is received within the second holder assembly; positioning a second spinal rod within the second holder assembly; and coupling a set screw to the second holder assembly to secure the second spinal rod in a desired position.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, various embodiments disclosed herein relate to a head over head connector assembly for facilitating the use of spinal rods or other stabilization devices to address degenerative conditions, deformity, trauma, tumor-induced conditions, and similar conditions that may impact the spine and/or surrounding areas. The embodiments disclosed herein enable placement and positioning of multiple spinal rods using holder assemblies (e.g., head assemblies, etc.) positioned "over" one another. For example, various embodiments enable placement of two spinal rods of varying material and/or diameter on either, or both, of the ipsilateral and contralateral sides of the spinal column. Two spinal rods may be required to provide additional support to an implanted construct (e.g., a bone screw/spinal rod construct). Placing two spinal rods side by side may be prohibited due to anatomical structures and/or limitations or other factors.

The embodiments disclosed herein are usable in a variety of applications, including a pedicle subtraction osteotomy (PSO), or surgical procedures used in adults or children to correct detain deformities of the spine. For example, when performing a PSO or similar procedure, a primary spinal rod and screw construct may be placed above and below the surgical site, and compressed to assist with repositioning of the bone. In some cases, a screw construct may be too low to allow for placement of a longer rod for other effected vertebrae, which would normally then require medial to lateral connectors to attach the PSO segment to the main construct. The embodiments herein enable placement of a PSO construct and a second spinal rod in line or over the top of each other.

Referring now to FIGS. 1-6, a spinal construct 10 (e.g., a construct assembly, etc.) is shown according to one embodiment. The spinal construct 10 includes a connector assembly 12, a first spinal rod 14, and a second spinal rod 16. Spinal construct 10 is in some embodiments usable to enable a user to place first and second spinal rods (e.g., of varying diameters) along various portions or sides of the spinal column and structurally couple the two spinal rods.

Figure 1:
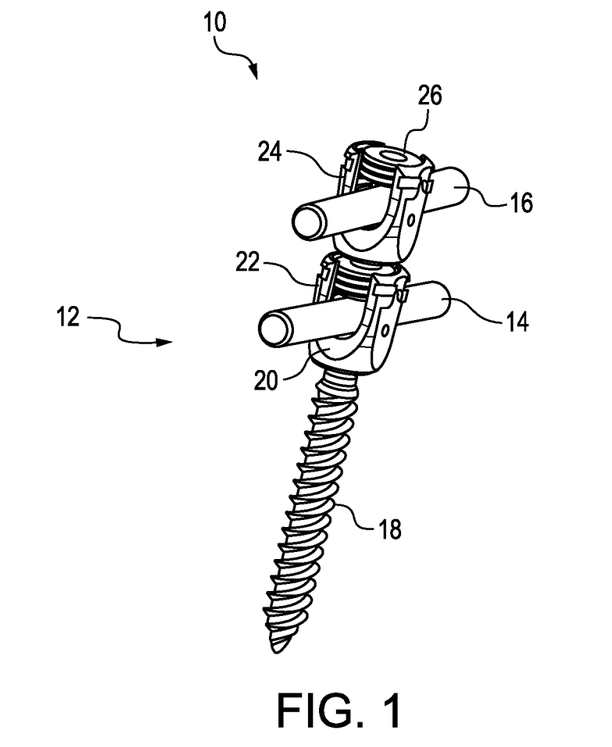
FIG. 1 is a perspective view of a spinal construct including a connector assembly for connecting multiple spinal rods according to one embodiment.
Figure 2:
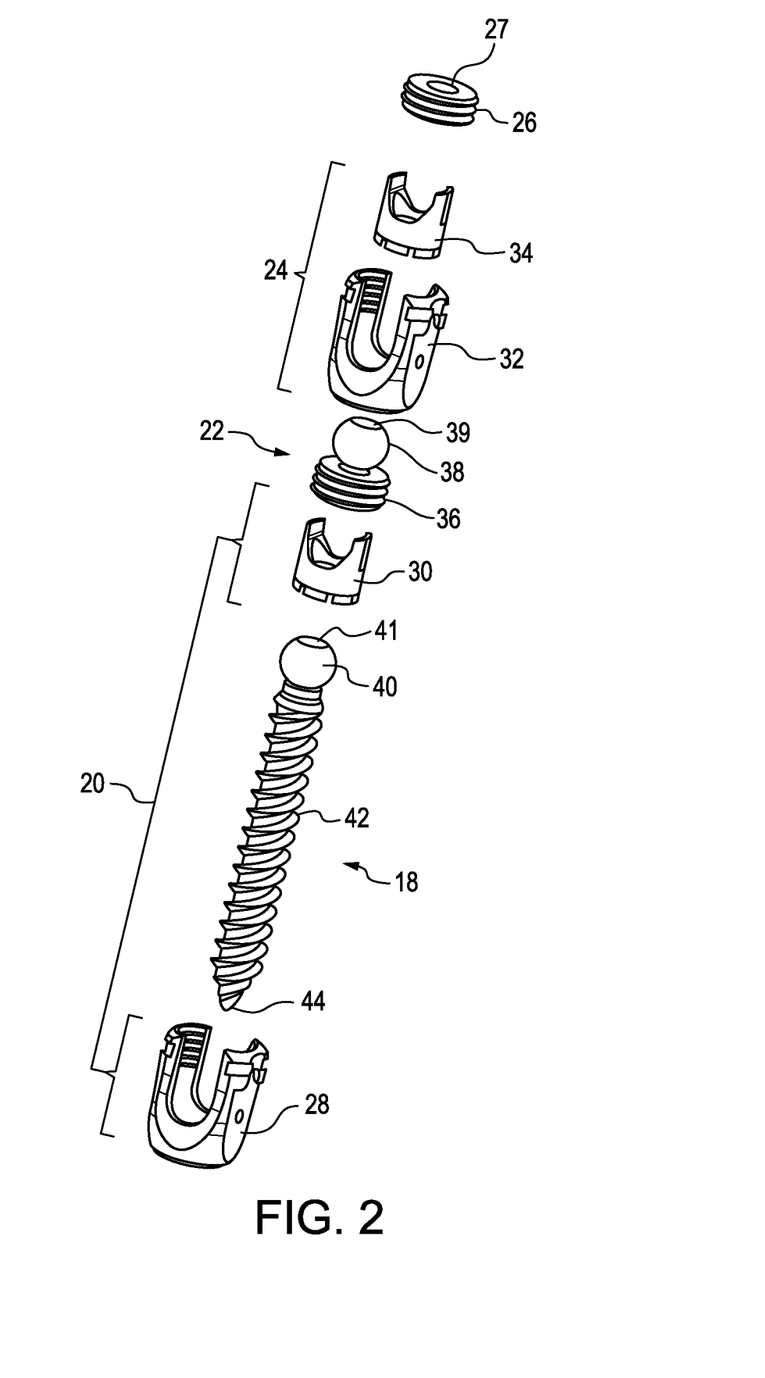
FIG. 2 is an exploded view of the connector assembly of FIG. 1 according to one embodiment.

Referring to FIG. 2, connector assembly 12 is shown according to one embodiment. The connector assembly 12 includes a bone screw 18, a first holder assembly 20, an extension set screw 22 (e.g., a first fastener), a second holder assembly 24, and a set screw 26 (e.g., a second fastener). The first holder assembly 20 secures the bone screw 18 in a desired position and receives the first spinal rod 14. The first holder assembly 20 further receives the extension set screw 22. The second holder assembly 24 secures the extension set screw 22 in a desired orientation and receives the second spinal rod 16. The second holder assembly 24 also receives the set screw 26 to maintain the second spinal rod 16 in a desired position.

The connector assembly 12 enables the first spinal rod 14 to be generally aligned with the second spinal rod 16 (e.g., in an "in-line" fashion, etc.). In some embodiments, the first and second spinal rods 14, 16 extend in a general parallel fashion to each other. In other embodiments, the first and second spinal rods 14, 16 are slightly offset because of the polyaxial nature of the bone screw 18 and the extension set screw 22.

In some embodiments, the bone screw 18 includes a head 40, a shank 42, and a tip 44. The head 42 has a generally globular shape and includes a socket 41 configured to receive a bone screw installation tool (e.g., a hex wrench, a screwdriver, etc.). The shape of the head 40 provides for polyaxial adjustment/placement of the bone screw 18 when received within the first holder assembly 20. The shank 42 extends between the head 40 and the tip 44. All or a portion of the shank 42 may be threaded or otherwise include retention features (e.g., barbs, etc.) to maintain the bone screw 18 in a desired position. For example, in some embodiments, the entirety or substantially all of shank 42 is threaded, while in other embodiments, one or more portions of shank 42 are unthreaded. In some embodiments, all or a portion of the shank 42 is tapered toward the tip 44 of the bone screw 18. Bone screw 18 is configured to enable a user to secure bone screw 18 to a portion of bone (e.g., a vertebrae), and may be made of any suitable material (e.g., a metal, such as titanium, stainless steel, etc.). While in one embodiment bone screw 18 and head 40 provide for polyaxial adjustment of bone screw 18, in alternative embodiments, bone screw 18 and head 40 may provide for other types of adjustment, including uniplanar adjustment, monoaxial adjustment, etc.

The first holder assembly 20 includes a holder 28 (e.g., a tulip head, a head, etc.) and a locking sleeve 30 (e.g., an insert, a collet, a locking member, a taper lock, etc.). The locking sleeve 30 is received within the holder 28 and secures the bone screw 18 in a desired orientation relative to the holder 28. In some embodiments, the bone screw 18 and locking sleeve 30 are both received from a top of the holder 28 (e.g., to form a preassembled bone screw assembly), while in other embodiments, the bone screw 18 may be received through a bottom of the holder 28 and the locking sleeve 30 received from a top of the holder 28 (e.g., in cases where the bone screw 18 is implanted separately, and the holder 28 and locking sleeve 30 subsequently coupled to the bone screw 18.

Figure 9:
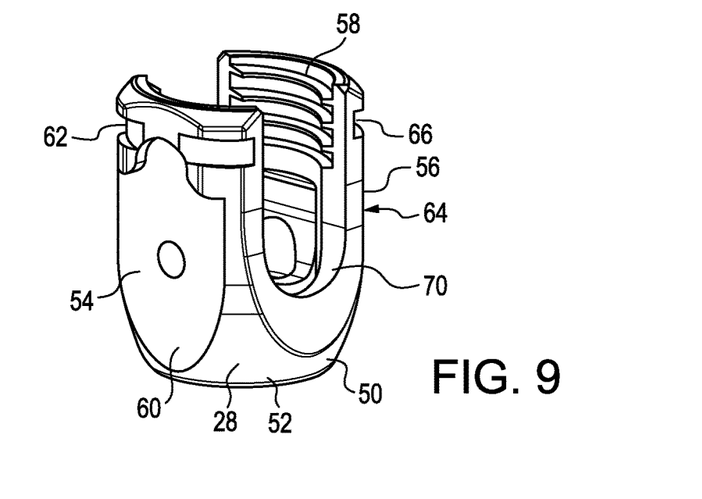
FIG. 9 is a perspective view of a holder assembly usable with the connector assembly of FIG. 1 according to one embodiment.
Figure 10:
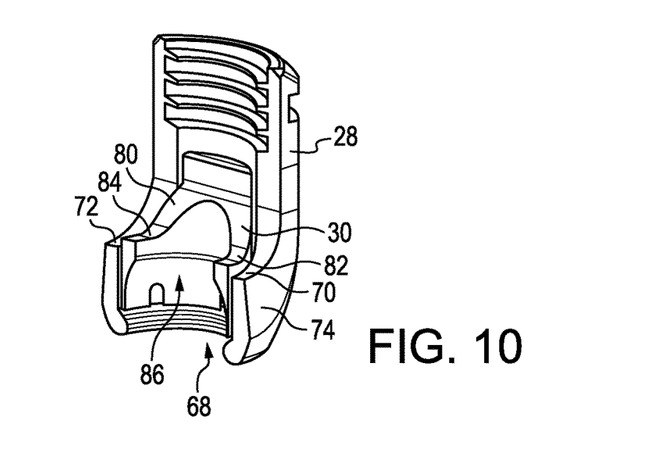
FIG. 10 is a cutaway perspective view of the holder assembly of FIG. 9 according to one embodiment.
Figure 11:
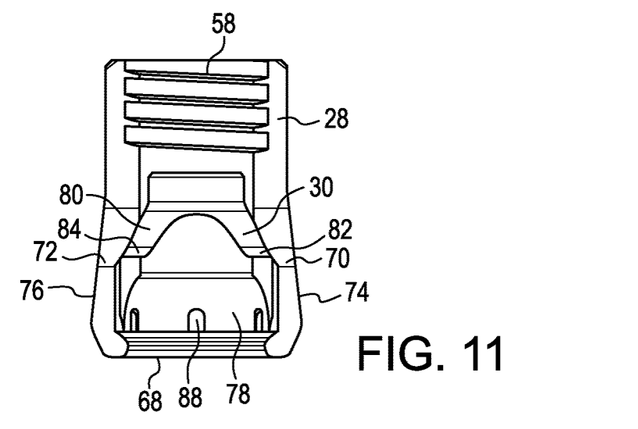
FIG. 11 is a cutaway side view of the holder assembly of FIG. 9 according to one embodiment.

Referring now to FIGS. 9-11, first holder assembly 20 is shown in greater detail according to one embodiment. In some embodiments, second holder assembly 24 has the same structure as first holder assembly 20. According to one embodiment, the holder 28 is defined by a generally tulip shaped body 50, having a bottom 52, a first side or sidewall 54, and a second side or sidewall 56. The second sidewall 54 is opposite the first sidewall 56. The first sidewall 54 and second sidewall 56 are arcuate in shape and include threads/threading 58 on an interior wall/surface. The internal threading 58 threadingly receives extension set screw 22 for fully seating the first spinal rod 14 in the holder 28. The first sidewall 54 has a first flat 60 on its exterior surface extending generally from proximate the top to the bottom 52. The first sidewall 54 further has first notches 62 on the lateral sides of the sidewall 54 proximate the top, permitting receipt of an installation tool. The second sidewall 56 has a second flat 64 on its exterior surface extending generally from proximate the top to the bottom 52. The second sidewall 56 further has second notches 66 on the lateral sides of the sidewall 56 proximate the top. Bottom 52 of the body 50 is generally rounded, for example, in portions adjacent first flat 60 and second flat 64.

The holder 28 has an interior bore 68 extending through the bottom 52 of the body 50. The bore 68 receives the bone screw 18 and the locking sleeve 30. A spine rod reception area is defined in the body 50, and formed as a first pocket, cutout or notch 70 between lateral sides of the first sidewall 54 and the second sidewall 56, and a second pocket, cutout or notch 72 between lateral sides of the first sidewall 54 and the second sidewall 56. The first and second notches 70, 72 are opposite one another. The first and second notches 70, 72 are formed to receive a spinal rod such as first spinal rod 14 or second spinal rod 16, and thus may be generally arcuate or cup-shaped. The outside of the body 50 of the holder 28 surrounding the first notch 70 is a flat 74, while the outside of the body 50 surrounding the second notch 72 is a flat 76. The internal threading 58 of the first and second sidewalls 54, 56, provide for reception of a set screw such as extension set screw 22 that is used to "lock up" the holder 28 on and relative to the bone screw 18 via the locking sleeve 30.

The locking sleeve 30 provides a taper lock and is defined by a generally cylindrical body having a base or skirt 78 on a lower portion thereof and a pair of upstanding flanges, sides or sidewalls 80 that define first and second pockets, cutouts or notches 82, 84 between lateral sides of the upstanding sidewalls 80. The first and second notches 82, 84 are formed to receive a spinal rod such as first spinal rod 14 or second spinal rod 16, and thus may be generally arcuate or cup-shaped. An interior bore 86 extends though the locking sleeve 30 and allows access to the socket 41 of the head 40 of the bone screw 18.

A bottom area of the locking sleeve 30 includes a plurality of cuts 88 (e.g., slits, cutouts, notches, slots, etc.) that extend axially upward from the bottom of locking sleeve 30 toward the upstanding flanges 80. In one embodiment, the cuts 88 are equally circumferentially spaced about the bottom area of the locking sleeve 30. In some embodiments, the cuts 88 create a collet mechanism that allows the head 40 of bone screw 18 to snap into the bottom area of the locking sleeve 30, thus creating a frictional interference fit. It should be appreciated that the number of cuts 88 may vary from two (2) to as many as desired. The cuts 88 may create a resilient or elastic interference or snap on fit with the screw head 40 by allowing the bottom area of locking sleeve 30 to splay slightly outward and then form back around the screw head 40. The spherical coverage of the head 40 increases the amount of surface contact between the bottom area of the locking sleeve 30 and the screw head 40. In some embodiments, locking sleeve 30 is forced downward relative to bone screw 18 and holder 28 (e.g., by threadingly advancing extension set screw 22 against first spinal rod 14), thereby securing bone screw 18 and first spinal rod 14 in a desired position.

Referring back to FIG. 2, the extension set screw 22 includes a head portion 38 and a set screw or threaded portion 36. The head portion 38 is similar to the head 40 of the bone screw 18, and includes a generally globular shape and a socket 39 configured to receive a bone screw installation tool (e.g., a hex wrench, a screwdriver, etc.). The shape of the head 38 provides for polyaxial adjustment/ placement of the extension set screw when received within the second holder assembly. The threaded portion 36 is received by the first holder assembly 20, and is usable to secure the first spinal rod 14 in a desired position. Integrating a head and set screw into the extension set screw 22 enables assembling the first holder assembly 20 and second holder assembly 24 in an in-line fashion (e.g., vertically aligned such that spinal rods may extend in a generally parallel fashion). While in one extension set screw 22 and head portion 38 provide for polyaxial adjustment of extension set screw 22, in alternative embodiments, extension set screw 22 and head portion 38 may provide for other types of adjustment, including uniplanar adjustment, monoaxial adjustment, etc.

The second holder assembly 24 may be the same or similar to the first holder assembly 20, and includes a holder 32 (e.g., a tulip head, a head, etc.) and a locking sleeve 34 (e.g., an insert, a collet, a locking member, a taper lock, etc.). The locking sleeve 34 is received within the holder 32 and secures the extension set screw 22 in a desired orientation relative to the holder 32. In some embodiments, the locking sleeve 34 is received from a top of the holder 32 (e.g., in the case of a preassembled holder assembly), while in other embodiments, the extension set screw 22 and the locking sleeve 30 are received from a bottom of the holder 32 (e.g., in cases where the extension set screw 22 is secured separately, and the holder 32 and locking sleeve 34 are subsequently coupled to the extension set screw 22).

The set screw 26 secures the second spinal rod 16 within the second holder assembly 24. The set screw 26 includes a socket 27 configured to receive an installation tool (e.g., a hex wrench, a screwdriver, etc.). In some embodiments, the bone screw 18, the extension set screw 22, and the set screw 26 are all configured to receive the same installation tool, such as a screw driver, etc. As such, the sockets on the bone screw 18, extension set screw 22, and set screw 26 may be identical and/or capable of receiving the same installation tool.

In one embodiment, first spinal rod 14 is an elongated member and may have a circular or other cross-sectional shape (e.g., oval, flat-sided, irregular, etc.). For example, first spinal rod 14 may have a flat portion configured to facilitate engagement with a fastener such as extension set screw 22. First spinal rod 14 may be made of any suitable material, including stainless steel, titanium, etc. Second spinal rod 16 in some embodiments is of identical or similar construction to first spinal rod 14. In further embodiments, second spinal rod 16 may of dissimilar construction or material to first spinal rod 14 (e.g., of different diameter, cross-sectional shape, etc.). For example, in one embodiment, first spinal rod 14 is generally circular in cross-section and has a first diameter, and second spinal rod 16 is generally circular in cross-section but has a second diameter different from the first diameter (i.e., smaller or larger).

Figure 3:
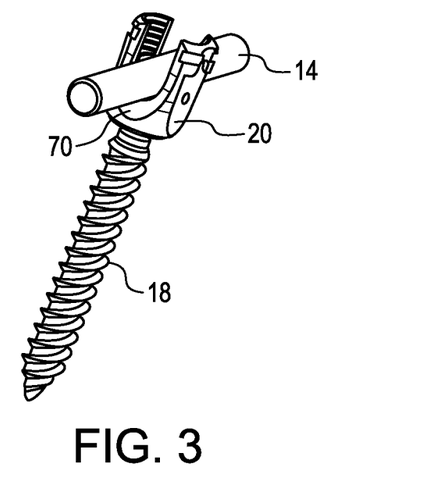
FIG. 3 is a perspective view of a portion of the connector assembly of FIG. 1 according to one embodiment.
Figure 4:
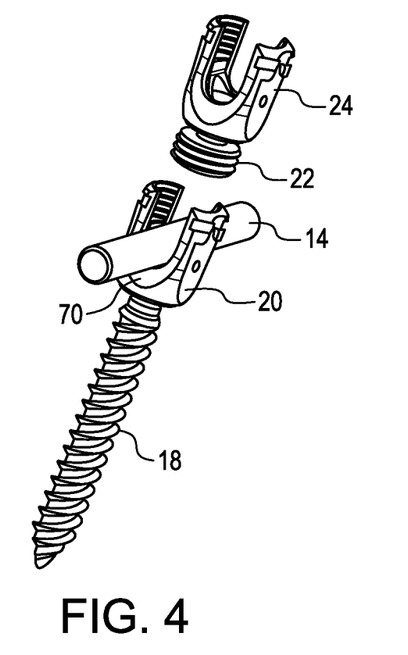
FIG. 4 is a partial exploded view of a portion of the connector assembly of FIG. 1 according to one embodiment.

Referring to FIGS. 3 and 4, a portion of connector assembly 12 is shown receiving first spinal rod 14 according to one embodiment. As shown in FIG. 3, after bone screw 18 is secured in bone and coupled to first holder assembly 20, the first spinal rod 14 is captured and aligned within first holder assembly 20 (e.g., received within first and second notches 70, 72 of holder 28). As discussed in greater detail herein, bone screw 18 may be coupled with first holder assembly 20 either prior to or after securing bone screw 18 to bone. As shown in FIG. 4, after first spinal rod 14 is provisionally seated within first holder assembly 20, extension set screw 22 may be threadingly coupled to holder 28 of first holder assembly. Extension set screw 22 may be coupled to second holder assembly 24 either prior to or after securing extension set screw 22 to first holder assembly 20.

Figure 5:
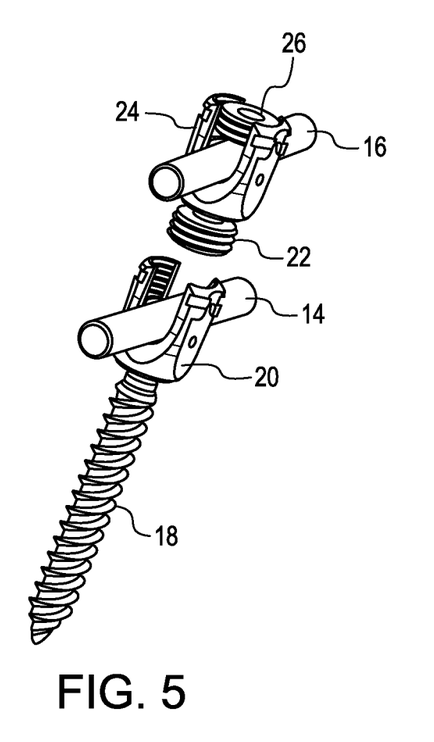
FIG. 5 is a partial exploded view of the connector assembly of FIG. 1 according to one embodiment.

Referring to FIG. 5, (showing extension set screw 22 decoupled from first holder assembly 20), upon securing extension set screw 22 and second holder assembly 24 to first holder assembly 20, the second spinal rod 16 is captured and aligned within second holder assembly 24 (e.g., received within first and second notches 70, 72 of a holder such as holder 28). After second spinal rod 16 is provisionally seated within second holder assembly 24, set screw 26 may be threadingly coupled to second holder assembly 24 to secure second spinal rod 16 in a desired position.

Figure 6:
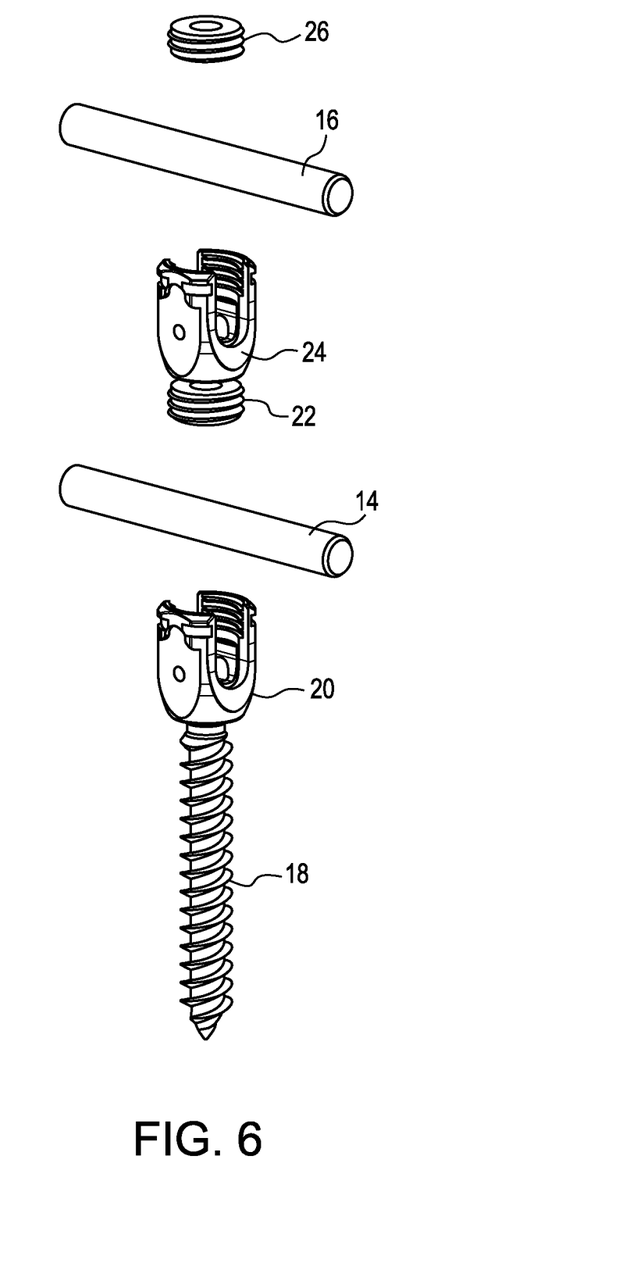
FIG. 6 is an exploded view showing certain components of the assembly of FIG. 1 preassembled according to one embodiment.

Referring now to FIG. 6, a first method of assembling connector assembly 12 is illustrated according to one embodiment. As shown in FIG. 6, prior to securing bone screw 18 to bone, bone screw 18 may be pre-assembled with first holder assembly 20 to form a pre-assembled bone screw assembly. After securing the bone screw 18 to bone, the first spinal rod 14 is provisionally seated within the first holder assembly 20. Prior to securing extension set screw 22 to first holder assembly 20, extension set screw 22 is coupled with second holder assembly 24 to form a head extender assembly. After securing extension set screw 22 to first holder assembly 20, second spinal rod 16 is provisionally seated within second holder assembly 24. After second spinal rod 16 is seated within second holder assembly 24, set screw 26 is secured to second holder assembly 26 for final tightening. In some embodiments, bone screw 18, extension set screw 22, and set screw 26 are all adjustable (e.g., to be tightened or loosened) using a single tool. For example, each component may have the same or similar socket to receive an end of an installation tool.

Figure 7:
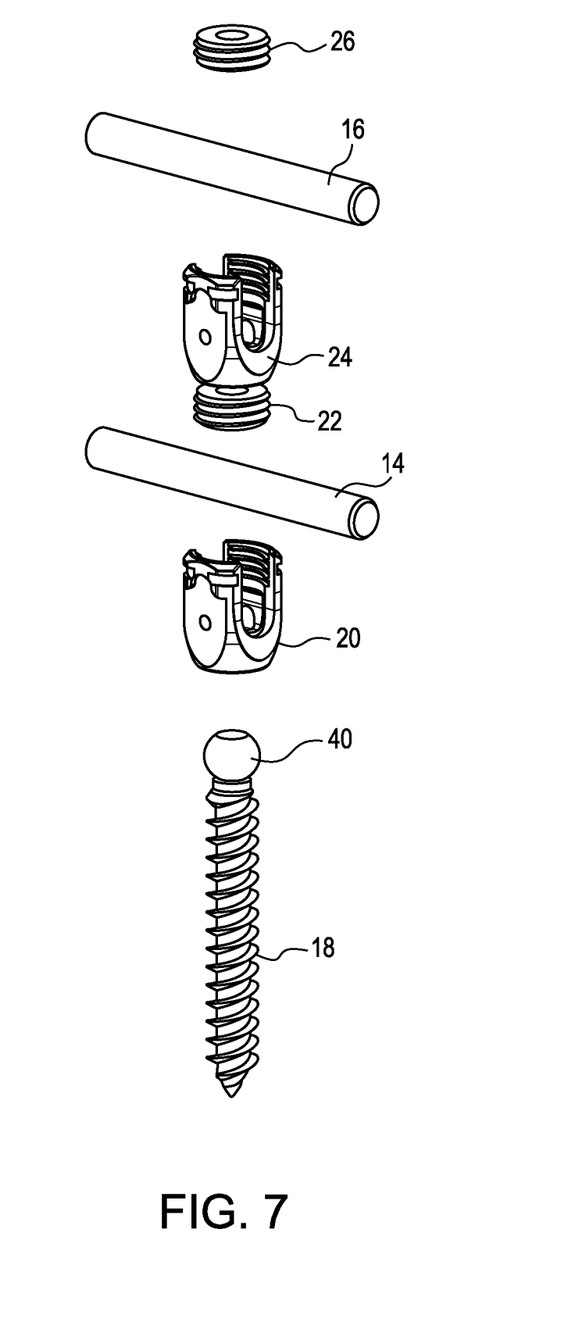
FIG. 7 is an exploded view showing certain components of the assembly of FIG. 1 preassembled according to another embodiment.

Referring to FIG. 7, a second method of assembling connector assembly 12 is illustrated according to one embodiment. The method shown in FIG. 7 is similar to that illustrated in FIG. 6, except that prior to securing bone screw 18 to bone, bone screw 18 is not pre-assembled with first holder assembly 20 to form a pre-assembled bone screw assembly. Rather, bone screw 18 is secured to bone, and the first holder assembly 20 is placed over the head 40 of bone screw 18 while bone screw 18 is secured to bone. The first spinal rod 14 is then provisionally seated within the first holder assembly 20. Prior to securing extension set screw 22 to first holder assembly 20, extension set screw 22 is coupled with second holder assembly 24 to form a head extender assembly. After securing extension set screw 22 to first holder assembly 20, second spinal rod 16 is provisionally seated within second holder assembly 24. After second spinal rod 16 is seated within second holder assembly 24, set screw 26 is secured to second holder assembly 26 for final tightening. In some embodiments, bone screw 18, extension set screw 22, and set screw 26 are all adjustable (e.g., to be tightened or loosened) using a single tool. For example, each component may have the same or similar socket to receive an end of an installation tool.

Figure 8:
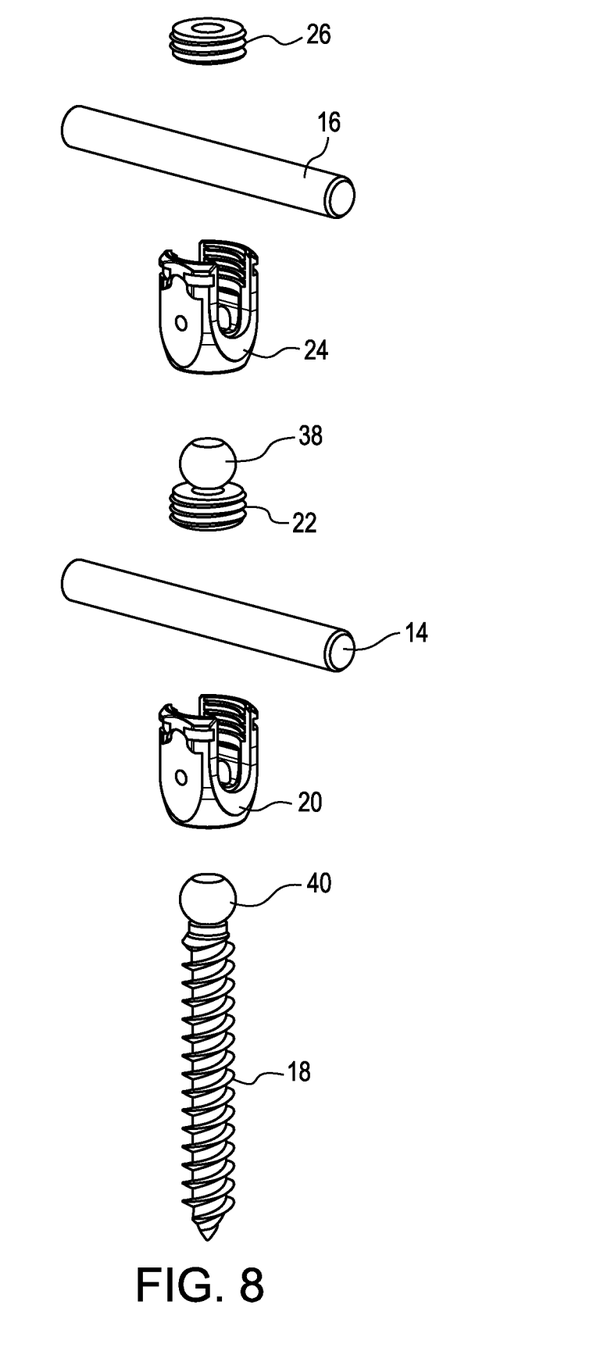
FIG. 8 is an exploded view showing certain components of the assembly of FIG. 1 preassembled according to another embodiment.

Referring to FIG. 8, a third method of assembling connector assembly 12 is illustrated according to one embodiment. The method shown in FIG. 8 is similar to that illustrated in FIG. 7 except that prior to securing extension set screw 22 to first holder assembly 20, extension set screw 22 is not coupled with second holder assembly 24 to form a head extender assembly Bone screw 18 is secured to bone, and the first holder assembly 20 is placed over the head 40 of bone screw 18 after bone screw 18 is secured to bone. The first spinal rod 14 is then provisionally seated within the first holder assembly 20. Extension set screw 22 is then secured to first holder 20, and second holder assembly 24 is placed over the head 38 of extension set screw 22. Second spinal rod 16 is then provisionally seated within second holder assembly 24. After second spinal rod 16 is seated within second holder assembly 24, set screw 26 is secured to second holder assembly 26 for final tightening. In some embodiments, bone screw 18, extension set screw 22, and set screw 26 are all adjustable (e.g., to be tightened or loosened) using a single tool. For example, each component may have the same or similar socket to receive an end of an installation tool.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

Although the figures and description may illustrate a specific order of method steps, the order of such steps may differ from what is depicted and described, unless specified differently above. Also, two or more steps may be performed concurrently or with partial concurrence, unless specified differently above. Such variation may depend, for example, on the systems chosen and on designer choice.

It is important to note that the construction and arrangement of the connector assembly as shown in the various exemplary embodiments is illustrative only. Additionally, any element disclosed in one embodiment may be incorporated or utilized with any other embodiment disclosed herein. For example, the first holder assembly may in some embodiments also be used as the second holder assembly. Although only one example of an element from one embodiment that can be incorporated or utilized in another embodiment has been described above, it should be appreciated that other elements of the various embodiments may be incorporated or utilized with any of the other embodiments disclosed herein.

What is claimed is:

1. A connector assembly, comprising:
    a bone screw comprising a head;
    a first holder assembly configured to receive the head of the bone screw from a bottom of the first holder assembly;
    an extension set screw comprising a head and a threaded portion, the threaded portion configured to be received from a top of the first holder assembly;
    a second holder assembly configured to receive the head of the extension set screw, wherein the second holder assembly includes a holder and a locking sleeve received within the holder, the locking sleeve configured to couple the second holder assembly to the extension set screw; and
    an end fastener configured to be received by the second holder assembly.

2. The connector assembly of claim 1, wherein the first holder assembly includes a first holder and a first locking sleeve received within the first holder, the first locking sleeve configured to resiliently receive the head of the bone screw from the bottom of the first holder assembly.

3. The connector assembly of claim 2, wherein the bone screw and the first holder assembly are configured to enable a user to secure the head of the bone screw within the first holder assembly while the bone screw is secured to bone.

4. The connector assembly of claim 1, wherein the head of the bone screw enables polyaxial movement of the head of the bone screw relative to the first holder assembly.

5. The connector assembly of claim 1, wherein the head of the extension set screw enables polyaxial movement of the head of the extension set screw relative to the second holder assembly.

6. The connector assembly of claim 1, wherein the first holder assembly and the second holder assembly are configured to secure first and second spinal rods in a generally parallel fashion.

7. The connector assembly of claim 1, wherein the second holder assembly is configured to receive the head of the extension set screw after the threaded portion of the extension set screw is received by the first holder assembly.

8. The connector assembly of claim 1, wherein the head of the bone screw comprises a first socket of a first shape, and the head of the extension set screw comprises a second socket of the first shape.

9. A connector assembly, comprising:
    a bone screw comprising a head;
    a first holder assembly configured to receive the head of the bone screw;
    an extension set screw comprising a head and a threaded portion, the threaded portion configured to be received by the first holder assembly;
    a second holder assembly configured to receive the head of the extension set screw, wherein the second holder assembly includes a holder and a locking sleeve received within the holder, the locking sleeve configured to couple the second holder assembly to the extension set screw;
    a set screw configured to be received by the second holder assembly;
    wherein the first holder assembly and the second holder assembly are configured to secure first and second spinal rods in a generally parallel fashion.

10. The connector assembly of claim 9, wherein the first holder assembly is configured to receive the head of the bone screw from a bottom of the first holder assembly.

11. The connector assembly of claim 10, wherein the first holder assembly includes a holder and a locking sleeve received within the holder, the locking sleeve configured to resiliently receive the head of the bone screw from the bottom of the first holder assembly.

12. The connector assembly of claim 10, wherein the bone screw and the first holder assembly are configured to enable a user to secure the head of the bone screw within the first holder assembly while the bone screw is secured to bone.

13. The connector assembly of claim 9, wherein the head of the bone screw enables polyaxial movement of the head of the bone screw relative to the first holder assembly.

14. The connector assembly of claim 9, wherein the head of the extension set screw enables polyaxial movement of the head of the extension set screw relative to the second holder assembly.

15. The connector assembly of claim 9, wherein the second holder assembly is configured to receive the head of the extension set screw after the threaded portion of the extension set screw is received by the first holder assembly.

16. The connector assembly of claim 9, wherein the locking sleeve further comprises a notch configured to received a spinal rod.

17. A method of assembling a connector assembly comprising:
    securing a bone screw to bone, the bone screw including a head and a threaded portion, the threaded portion configured to engage the bone;
    coupling a first holder assembly to the hone screw, wherein the head of the bone screw is received within the first holder assembly, wherein the first holder assembly includes a holder and a locking sleeve received within the holder, the locking sleeve configured to secure the bone screw in a first position relative to the first holder assembly;
    positioning a first spinal rod within the first holder assembly;
    coupling an extension set screw to the first holder assembly to secure the first spinal rod in a desired position, the extension set screw comprising a head and a threaded portion, the threaded portion configured to threadingly engage the first holder assembly;
    coupling a second holder assembly to the extension set screw, wherein the head of the extension set screw is received within the second holder assembly, wherein the second holder assembly includes a second holder and a second locking sleeve received within the second holder, the second locking sleeve configured to secure the extension set screw in a second position relative to the second holder assembly;
    positioning a second spinal rod within the second holder assembly; and
    coupling a set screw to the second holder assembly to secure the second spinal rod in a desired position.

18. The method of claim 17, further comprising aligning the second spinal rod in a generally parallel and aligned fashion with the first spinal rod.

19. The method of claim 17, wherein the first holder assembly is coupled to the bone screw after the bone screw is secured to the bone.

20. The method of claim 17, wherein the second holder assembly is coupled to the extension set screw after the extension set screw is coupled to the first holder assembly.

* * * * *